United States Patent [19]

Habich

[11] 4,314,030
[45] Feb. 2, 1982

[54] TEST TUBE FOR THE EXAMINATION OF URINE SAMPLES

[75] Inventor: Hans-Joachim Habich, Hildrizhausen, Fed. Rep. of Germany

[73] Assignee: C. A. Greiner & Söhne GmbH, Nürtingen, Fed. Rep. of Germany

[21] Appl. No.: 123,930

[22] Filed: Feb. 25, 1980

[51] Int. Cl.$^3$ ............................................. C12M 1/24
[52] U.S. Cl. ..................................... 435/296; 435/14; 435/27; 435/28
[58] Field of Search .......................... 422/57, 61, 102; 435/14, 27, 28, 296, 299, 300, 301

[56] References Cited

U.S. PATENT DOCUMENTS

| | | | |
|---|---|---|---|
| 2,865,718 | 12/1958 | Fowler | 422/57 X |
| 3,798,001 | 3/1974 | Naumann et al. | 422/57 X |
| 3,898,982 | 8/1975 | Katsuda | 422/57 X |
| 3,944,471 | 3/1976 | Waters | 435/35 |
| 4,022,578 | 5/1977 | Kretschmer | 422/57 |

FOREIGN PATENT DOCUMENTS

| | | | |
|---|---|---|---|
| 1037725 | 8/1958 | Fed. Rep. of Germany | 422/57 |
| 52-25359 | 8/1975 | Japan | 422/57 |

Primary Examiner—Robert J. Warden
Attorney, Agent, or Firm—Peter K. Kontler

[57] ABSTRACT

A test tube for the examination of samples, especially of urine samples, in clinical environment for the amount of a given ingredient in the sample, by contacting the sample with a first reagent that reacts with the ingredient in a reaction in which hydrogen peroxide is formed, and with a second reagent which, in cooperation with the so formed hydrogen peroxide, causes an indicator dye to change its color for indicating the amount of the ingredient in the sample, comprises catalase and oxidase contained in at least one layer on at least a part of the inner surface of the test tube, and a solid substance that releases oxygen under the influence of the catalase in the interior of the test tube, the oxidase acting to cause oxidation by the released oxygen of any other ingredient (such as ascorbic acid) of the sample (such as urine sample) which would otherwise react with the formed hydrogen peroxide and thus deleteriously influence the indicator dye color change.

10 Claims, 2 Drawing Figures

TEST TUBE FOR THE EXAMINATION OF URINE SAMPLES

BACKGROUND OF THE INVENTION

The present invention relates to a test tube for the examination of samples in general, and more particularly to a test tube for the examination of urine samples for the amount of glucose present therein, particularly in clinical environment.

In this connection, it is already known to contact the sample with a first reagent that reacts with an ingredient the amount of which is to be established in a reaction in which hydrogen peroxide is formed, and with a second reagent which, in cooperation with the so formed hydrogen peroxide, causes an indicator dye to change its color for indicating the amount of the ingredient in the sample.

An example of such an examination is the examination of urine for the glucose contents thereof by means of a testing strip. In this case, the first reagent is glucose oxidase which oxidizes the glucose to δ-gluconolactone in the presence of oxygen (in the ambient air). During this reaction, hydrogen peroxide (H₂O₂) is released. This reaction is as follows:

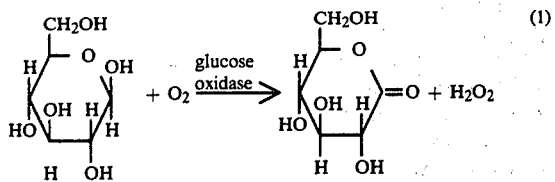

The hydrogen peroxide which is formed during this reaction (1) oxidizes, for instance, a colorless indicator dye which changes or develops its color during its oxidation, such as, for instance, a colorless chromogen, for instance, o-tolidine which, when oxidized, acquires a blue color. This reaction takes place in the presence of peroxidase as follows:

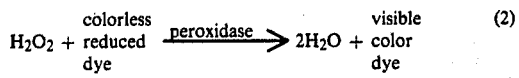

It is also known (compare, for instance, Kohl, Störungen der Glucose-Anzeige durch Ascorbinsäure bei Teststreifen, Laboratoriumsblätter 27 (1977), pp 103–108) that the presence of ascorbic acid in the urine sample leads to inaccurate or totally false negative results, inasmuch as the hydrogen peroxide which is released during the oxidation of glucose to δ-gluconolactone and the amount of which determines, after the reaction (2), the degree of the coloring of the testing strip, reacts with the ascorbic acid and oxidizes the same to dehydroascorbic acid, which latter is a colorless substance. This reaction takes place as follows:

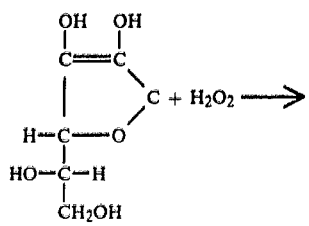

-continued

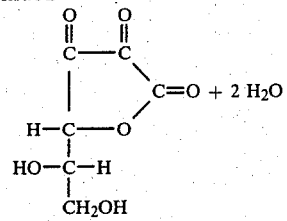

This, consequently, means that the hydrogen peroxide which develops in the course of the reaction (1) is consumed by the reaction (3) with the ascorbic acid, so that the so consumed hydrogen peroxide is unavailable for causing a change in the color of the indicator dye and thus for the indication of the presence of glucose in the urine sample. This, of course, means that the presence and amount of glucose in the urine sample is not indicated at all, or is not indicated to a degree corresponding to the actual condition.

This problem has already been recognized before and, in order to eliminate this error during the determination of glucose content by means of a testing strip, it has been proposed (see, for instance, page 105 of the above publication) to additionally provide an ascorbic acid testing area in the testing strip, so that the evaluation of urine samples which contain ascorbic acid can be avoided. However, this method leads merely to the recognition of such urine samples which are unsuited for the performance of the rapid test using the testing strip, and cannot be used to determine the actual amount of glucose in such urine samples.

OBJECTS AND SUMMARY OF THE INVENTION

Accordingly, it is a general object of the present invention to avoid the disadvantages of the prior art. More particularly, it is an object of the present invention to provide a testing tube for the examination of samples, which renders it possible to obtain accurate indications despite the presence in the sample of ingredients which would react with hydrogen peroxide during the testing operation.

Still more particularly, it is an object of the present invention to develop a test tube for the examination of a urine sample in which the conventional glucose test can be performed with the aid of a testing strip without obtaining erroneous indications, even though the urine sample may contain ascorbic acid.

A concomitant object of the present invention is to provide a testing tube of the type here under consideration which is simple in construction, inexpensive to manufacture, and reliable nevertheless.

In pursuance of these objects and others which will become apparent hereafter, one feature of the present invention resides in a test tube for the examination of samples, especially of urine samples in clinical environment for the amount of a given ingredient in the sample, by contacting the sample with a first reagent that reacts with the ingredient in a reaction in which hydrogen peroxide is formed, and with a second reagent which, in cooperation with the so-formed hydrogen peroxide, causes an indicator dye to change its color (such as from colorless to a particular color) for indicating the amount of the ingredient in the sample, which test tube comprises, briefly stated, catalase and oxidase contained in at least one layer on at least a part of the inner surface of the test tube, and a solid substance that releases oxygen under the influence of the catalase in the interior of the test tube, the oxidase acting to cause oxidation by the released oxygen of any other ingredient of the sample which would otherwise react with the formed hydrogen peroxide and thus deleteriously influence the indicator dye color change.

A currently preferred embodiment of the present invention is a test tube for the examination of urine samples which may contain ascorbic acid as the other ingredient, with the aid of a glucose testing strip containing glucose oxidase as the first reagent and peroxidase as the second reagent. Under these circumstances, the aforementioned substance which releases oxygen under the influence of catalase is preferably peroxide and the oxidase is ascorbic acid oxidase. As soon as the urine sample is introduced into the test tube, the catalase forms oxygen and water from the peroxide, in accordance with the following reaction:

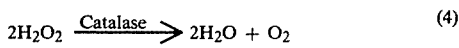

$$2H_2O_2 \xrightarrow{\text{Catalase}} 2H_2O + O_2 \qquad (4)$$

This reaction takes place only upon the introduction of the urine sample into the test tube, inasmuch as the catalase, which forms the aforementioned layer with the ascorbic acid oxidase, on the one hand, and the peroxide, on the other hand, are dry and situated at separate locations in the test tube. Consequently, the reaction (4) takes place only after the urine sample has been introduced into the test tube.

Now, the oxygen which is released during the reaction (4) oxidizes, in the presence of the ascorbic acid oxidase, the ascorbic acid to dehydroascorbic acid in accordance with the following reaction:

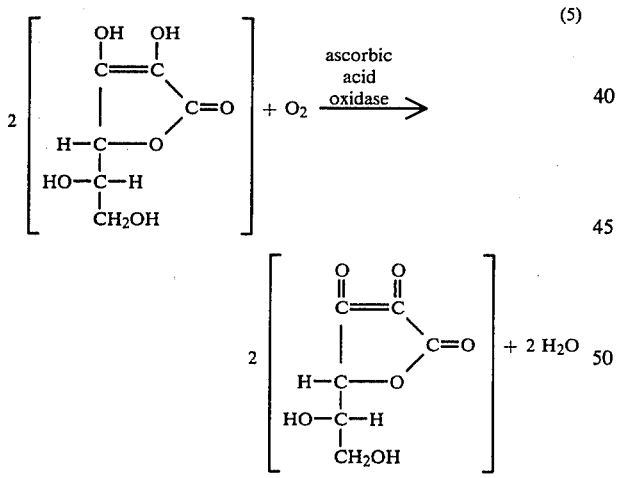

As a result of this construction of the test tube, the ascorbic acid present in the urine sample is so reacted that the resulting oxidation product, that is, the dehydroascorbic acid, can no longer react with the hydrogen peroxide which is obtained during the reaction (1) which is a part of the examination for glucose. Of course, a precondition for this is that the catalase is present in the test tube in such an amount that it converts the entire amount of peroxide which is present in the test tube in the course of the reaction (4).

The novel features which are considered as characteristic of the invention are set forth in particular in the appended claims. A test tube for the examination of urine samples itself, however, both as to its construction and its mode of operation, together with additional features and advantages thereof, will be best understood upon perusal of the following detailed description of certain specific embodiments with reference to the accompanying drawing.

DETAILED DESCRIPTION OF THE PREFERRED EMBODIMENTS

Figures 1, 2:
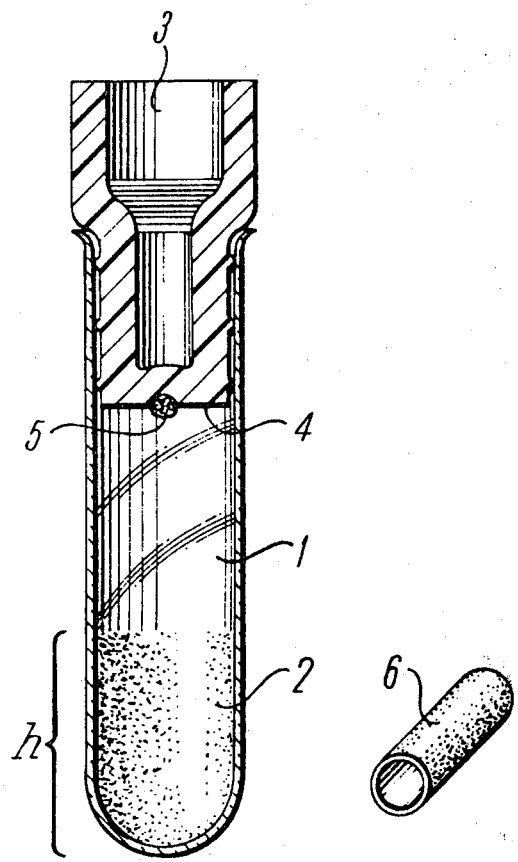
FIG. 1 is a longitudinal sectional view of a test tube according to the present invention.
FIG. 2 is a perspective view of a tubular carrier body which may be used in the test tube of FIG. 1.

Referring now to the drawing in detail, and first to FIG. 1 thereof, it may be seen that the reference numeral 1 has been used to identify an apertured vessel shown here as a test tube in accordance with the present invention. The inner surface of the test tube 1 is provided with a layer 2, commencing at the bottom of the test tube 1 and extending to the height h from the bottom. The layer 2 includes catalase and ascorbic oxidase. The test tube 1 has an upper open end which is closed at least during the use of the test tube 1, by closure means shown here as a plug 3 which has an end face 4 which delimits the internal cavity of the test tube 1 when the plug 3 is introduced into the open upper end of the latter. A body 5 of peroxide is provided at the end face 4. The body 5 has a shape of a heap or a globule which adheres to the end face 4 of the plug 3. The body 5 of peroxide may be obtained by either letting a solution of peroxide dry on the end face 4, or by gluing the body 5 in its dry condition to the end face 4 by a suitable soluble substance, such as gelatin.

When a urine sample is introduced into the test tube, followed by introduction of the plug 3 into the open upper end of the test tube 1, the layer 2 becomes dissolved in the urine sample first. Thereafter, the plugged test tube 1 can be tilted so that the urine sample contacts the body 5 and dissolves the peroxidase. When this happens, the aforementioned reactions (4) and (5) take place in the urine sample contained in the test tube 1. After these reactions have taken place, the plug 3 can be removed and a conventional testing strip can be introduced into the test tube 1, so that the reactions (1) and (2) can take place thereon for the determination of the glucose contents of the urine sample, without encountering the danger that the test results would be influenced or negatively falsified by the disturbing reaction (3).

The layer 2 may be formed, for instance, in the following manner: 75 mmol of a buffer solution, for instance, a tris(hydroxymethyl) aminomethane hydrochloride is dissolved in one liter of water. This solution is brought to pH 5.6 by the addition of citric acid. This value has been found to be especially advantageous for the reaction of the ascorbic acid oxidase.

After this buffer solution has been formed, the catalase is dissolved therein. This substance is readily available on the market. 1000 mg of catalase is dissolved in one liter of the buffer solution.

Furthermore, 500 mg of ascorbic acid oxidase is dissolved in 1 liter of the buffer solution. The production of this substance is known (for instance, from Hoppe-Seyler/Thierfelder, Handbuch der physiologisch-und pathologischchemischen Analyse, 10th, Ed., 1964 p.

909 ff, or as indicated in Boyer, Lardy, Myrbäck (Publisher), The Enzymes, 2. Ed., Vol. 8, New York and London (1963), p. 297 ff.).

Approximately 20 microliters of this solution is needed for approximately 15 milliters of a urine sample. Assuming that the capacity of the test tube 1, as usual, is about 15 milliters, the layer 2 on the internal surface of the test tube 1 is formed from approximately 20 microliters of this solution which is constituted by the so obtained buffer/enzyme mixture. This can be achieved, for instance, by resorting to the use of an arrangement which is introduced into the interior of the test tube 1 through the open upper end thereof and which operates, at least in principle, in the manner of a spray gun. This arrangement is preferably so constructed as to meter the quantity of the solution which is sprayed onto the internal surface of the test tube 1 to form the layer 2 and to limit this amount to the desired value. Thus, these 20 microliters of the buffer/enzyme mixture are sprayed onto the internal surface of the test tube 1 and, thereafter, the test tube 1 is allowed to dry so as to obtain a layer 2. The fine spray mist which has become deposited on the internal surface of the test tube 1 thus dries and forms the dry layer 2 extending from the bottom to the height h on the internal surface of the test tube 1.

Now, it is still necessary to provide the body 5 of peroxide. A suitable peroxide, for instance, carbamide peroxide ($CO(NH_2)_2.H_2O_2$), is available on the market. As already mentioned before, the amount of peroxide, will be such that it is completely converted by the catalase. When the amount of catalase and ascorbic acid oxidase is selected in the above-mentioned manner, then the amount of peroxide is to be approximately 3 mgs. In the embodiment which is illustrated in FIG. 1, this amount of peroxide is applied in a partially concentrated form, that is, in the form of the body 5 provided at the lower end face 4 of the plug 3.

However, it is to be understood that the peroxide can be introduced into the interior of the test tube 1 in many other ways, such as those which are contamplated by the present invention and which will now be discussed.

It is possible to simply pour the peroxide in its pulverulent form into the interior of the test tube 1. Under these circumstances, the peroxide powder deposits as a layer at the bottom of the test tube 1, or it becomes distributed substantially uniformly along the internal surface of the test tube 1, for instance, due to electrostatic adhesion or the like. The amount of the peroxide is so minute that, in principle, there is no reason to fear that the peroxide could fall out of the test tube 1 when the latter is opened. However, it is also possible to dissolve the peroxide in water or to suspend the same in alcohol and to deposit the resulting suspension or solution on the inner surface of the test tube 1 or on the end face 4 of the plug 3 in this form. When this layer is to be formed on the internal surface of the test tube 1, it is preferably deposited at an area of the internal surface of the test tube 1 which is not already provided with the layer 2. However, it is possible, at least theoretically, to form this layer of peroxide over the layer 2, provided that the substances of the two layers are precluded, in one way or another, from reacting with each other during the application of the layer of peroxide.

A further possibility of introducing the peroxide into the interior of the test tube 1 would be to introduce the peroxide into the interior of the test tube 1 in rapidly dissolvable gelatin capsule. Another appearing possibility is to deposit or otherwise form a layer of the peroxide on a carrier member, such as a tubular carrier member 6 which is shown in FIG. 2 (for instance, by spraying a layer of the peroxide solution or suspension onto the tubular carrier member 6 and subsequent drying of this layer in the manner discussed above). Then, this tubular carrier member 6 provided with the layer of peroxide is inserted into the interior of the test tube 1. Thus, the test tube 1 of the illustrated construction, but with the tubular carrier member 6 instead of the body 5, constitutes a viable alternative embodiment of the present invention.

When the peroxide is introduced into the interior of the test tube 1 in such a manner that it is first dissolved and then applied to a selected location or sprayed over a selected area and subsequently dried, then the applicable solution may be obtained, for instance, by dissolving 3 mgs. of the peroxide in approximately 5 microliters of water.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptions should and are intended to be comprehended within the meaning and range of equivalence of the claims.

I claim:

1. A test tube for the examination of samples, especially of urine samples, for the amount of a given ingredient in the sample, comprising catalase and oxidase contained in at least one layer on at least a part of the inner surface of the test tube, and a solid peroxide substance received in the interior of the test tube, introduction of the sample into the test tube entailing dissolution of said layer and said substance which are present in sufficient amounts whereby the peroxide thus releases sufficient oxygen under the influence of the catalase in the interior of the test tube, the oxidase acting to cause oxidation by the released oxygen of any other ingredient of the sample which would otherwise deleteriously influence subsequent examination of the sample for the given ingredient.

2. A test tube as defined in claim 1 for the examination of urine samples possibly containing ascorbic acid as the other ingredient wherein said oxidase is ascorbic acid oxidase.

3. A test tube as defined in claim 1, wherein said peroxide substance is present in the test tube in the form of a dry powder.

4. A test tube as defined in claim 1; and further comprising a carrier member accommodated in the test tube; and wherein said peroxide substance is included in a layer on said carrier member.

5. A test tube as defined in claim 1; and further comprising means for closing the open end of the test tube, including a plug having an end face facing the interior of the test tube; and wherein said peroxide substance constitutes a layer on said end face.

6. A test tube for elimination of inaccurate examination results attributable to the presence of ascorbic acid in a urine sample being examined to determine the amount of glucose therein comprising first and second portions respectively having first and second surfaces in the interior of the tube, a coherent first discrete layer comprising catalase and ascorbic acid oxidase on said first surface and a coherent second discrete layer comprising peroxide on said second surface, introduction of the sample into the test tube entailing dissolution of said layers which are present in sufficient amounts whereby the second layer thus releases sufficient oxygen under the influence of the catalase and the oxygen oxidizes any ascorbic acid in the sample in the presence of the ascorbic acid oxidase such that the resulting dehydroascorbic acid will not affect the results of the subsequent glucose examination.

7. The test tube of claim 6 wherein said first and second portions are separable, said first portion comprising an apertured vessel and said second portion comprising means for closing said apertured vessel.

8. The test tube of claim 7 wherein said closure means comprises a plug and said second surface comprises a face of said plug facing the interior of said vessel when said vessel and said closure means are joined and said vessel is thereby sealed.

9. The test tube of claim 6 wherein said first and second portions are separable, said first portion comprising an apertured vessel and said second portion comprising a carrier member received in the interior of said vessel.

10. The test tube of claim 6 wherein said first and second portions are discrete sections of an apertured vessel.

* * * * *

UNITED STATES PATENT AND TRADEMARK OFFICE
CERTIFICATE OF CORRECTION

PATENT NO. : 4,314,030
DATED : February 2, 1982
INVENTOR(S) : Hans-Joachim HABICH It is certified that error appears in the above-identified patent and that said Letters Patent are hereby corrected as shown below:

Foremost page, item [30] Foreign Application Priority Data has been omitted. Should be inserted --Feb. 27, 1979 [DE] Federal Republic Germany 2907628--.

Col. 5, line 41, "contamplated" should read --contemplated--.

Col. 6, line 26, "adaptions" should read --adaptations--.

Signed and Sealed this

Twenty-eighth Day of June 1983

[SEAL]

Attest:

GERALD J. MOSSINGHOFF

Attesting Officer   Commissioner of Patents and Trademarks